United States Patent
Dijkstra et al.

(10) Patent No.: US 11,377,462 B2
(45) Date of Patent: Jul. 5, 2022

(54) PROCESS FOR THE PURIFICATION OF A NEUTRAL HUMAN MILK OLIGOSACCHARIDE (HMO) FROM MICROBIAL FERMENTATION

(71) Applicant: FrieslandCampina Nederland B.V., Amerfoort (NL)

(72) Inventors: Zwaantje Johanna Dijkstra, Amerfoort (NL); Franciscus Johannes Hubertus Jeurissen, Amerfoort (NL); Martina Henrica Maria Van Genuchten, Amerfoort (NL); Jacob Huisman, Amerfoort (NL)

(73) Assignee: FRIESLANDCAMPINA NEDERLAND B.V., Amerfoort (NL)

(*) Notice: Subject to any disclaimer, the term of this patent is extended or adjusted under 35 U.S.C. 154(b) by 68 days.

(21) Appl. No.: 16/643,983

(22) PCT Filed: Sep. 28, 2018

(86) PCT No.: PCT/EP2018/076392
§ 371 (c)(1),
(2) Date: Mar. 3, 2020

(87) PCT Pub. No.: WO2019/063757
PCT Pub. Date: Apr. 4, 2019

(65) Prior Publication Data
US 2021/0061835 A1     Mar. 4, 2021

(30) Foreign Application Priority Data
Sep. 29, 2017    (EP) .................................. 17194188

(51) Int. Cl.
| | |
|---|---|
| C07H 1/08 | (2006.01) |
| A23L 33/125 | (2016.01) |
| A23L 33/21 | (2016.01) |
| A23L 33/00 | (2016.01) |
| A23C 9/142 | (2006.01) |
| A23C 9/146 | (2006.01) |
| A23C 9/20 | (2006.01) |
| C07H 3/06 | (2006.01) |
| C12P 19/04 | (2006.01) |
| C12P 19/18 | (2006.01) |

(52) U.S. Cl.
CPC ............... *C07H 1/08* (2013.01); *A23C 9/146* (2013.01); *A23C 9/1422* (2013.01); *A23C 9/206* (2013.01); *A23L 33/125* (2016.08); *A23L 33/21* (2016.08); *A23L 33/40* (2016.08); *C07H 3/06* (2013.01); *C12P 19/04* (2013.01); *C12P 19/18* (2013.01); *A23V 2002/00* (2013.01)

(58) Field of Classification Search
None
See application file for complete search history.

(56) References Cited

U.S. PATENT DOCUMENTS

2016/0237104 A1*   8/2016   Jennewein ................ A61P 1/00

FOREIGN PATENT DOCUMENTS

WO    WO-2015/106943 A1    7/2015

OTHER PUBLICATIONS

International Search Report received in corresponding International Application No. PCT/EP2018/076392 dated Dec. 12, 2018, 3 pages.

* cited by examiner

*Primary Examiner* — Christian L Fronda
(74) *Attorney, Agent, or Firm* — Foley & Lardner LLP; Sunit Talapatra

(57) ABSTRACT

The invention relates to a process for the purification of a neutral human milk oligosaccharide (HMO) from a fermentation broth, the process comprising the steps of: (i) separating biomass from the fermentation broth to provide a crude solution; (ii) treating the crude solution with: (a) a cation-exchange material; (b) an anion-exchange material; and (c) a cation-exchange adsorbent resin; thereby obtaining a purified solution containing the neutral human milk oligosaccharide. Further, the invention relates to a process for fermentatively producing HMO in a fermentation broth and purifying the HMO from the broth.

23 Claims, No Drawings

PROCESS FOR THE PURIFICATION OF A NEUTRAL HUMAN MILK OLIGOSACCHARIDE (HMO) FROM MICROBIAL FERMENTATION

CROSS-REFERENCE TO RELATED APPLICATIONS

This application is the National Phase of International Patent Application No. PCT/EP2018/076392, filed Sep. 28, 2018, published on Apr. 4, 2019 as WO 2019/063757 A1, which claims priority to European Patent Application No. 17194188.3, filed Sep. 29, 2017. The contents of these applications are herein incorporated by reference in their entirety.

The invention relates to a process for the purification of a neutral human milk oligosaccharide (HMO).

Human milk contains various oligosaccharides (HMO's) which are important for a healthy development of infants. Many HMO's serve an important role in the development of a healthy intestinal microbiome. It is possible to chemically synthesize HMO's. However, such process has technical and economic limitations. WO 2012/112777 provides a fermentative process for producing HMO's in a bacterium. For 2'-fucosyllactose (2'-FL) a purification process is described, comprising product capture on coarse carbon column and elution with an organic solvent to obtain a eluate, followed by evaporation of the solvent to obtain a crude sugar product (a syrup or dry product). The sugar product is then subjected to flash chromatography on fine carbon and ion exchange media. The need for flash chromatography is disadvantageous, in particular when the purification is to be carried out on an industrial scale.

WO 2015/106943 refers to further enzymatic and fermentative methods to produce HMO's and observes that processes in the state of the art for purifying individual oligosaccharide products from complex mixtures (such as fermentation broths) are technically complex and uneconomical for food applications. According to WO 2015/106943, e.g. gel-filtration chromatography cannot be efficiently scaled up and is unsuitable for continuous operation. WO 2015/106943 further refers to the need to provide oligosaccharide products from which recombinant DNA or protein has been efficiently removed. According to the examples, a purity for 2'-FL of 94% at a yield of approximately 70% could be obtained by a purification process comprising the subsequent steps of: separation of biomass from the fermentation medium (comprising 2'-FL) by ultrafiltration using a filter membrane with a 10 kDa cut-off, passing the fermentation medium over a strong cationic ion exchanger to remove positive charged contaminants, directly followed by passing the fermentation medium over a strong anionic ion exchanger column. The thus obtained solution was then diafiltered and thereafter further concentrated by nanofiltration. The concentrated 2'-FL-solution was then treated with activated carbon to remove colorgiving material such as Maillard reaction products and aldol reaction products. Next the concentrated 2'-FL solution was subjected to electrodialysis and concentrated to obtain a 45% 2'-FL solution, which was again treated with ion exchangers, activated carbon and electrodialysis.

There is a need for an alternative purification process that provides a neutral HMO product in satisfactory yield and purity, in particular such process that does not require electrodialysis and/or that does not require a repetition of ion exchange and adsorption steps.

It has now been possible to obtain an HMO product in a satisfactory yield and purity from a fermentation broth wherein the HMO has been produced fermentatively.

Accordingly, the present invention relates to a process for the purification of a neutral human milk oligosaccharide (HMO) from a fermentation broth, the process comprising the steps of:
(i) separating biomass from the fermentation broth to provide a crude solution;
(ii) treating the crude solution with:
  a cation-exchange material;
  an anion-exchange material; and
  a cation-exchange adsorbent resin;
thereby obtaining a purified solution containing the neutral human milk oligosaccharide.

The invention further relates to a method for producing a neutral human milk oligosaccharide, comprising producing the neutral human milk oligosaccharide by microbial fermentation in a fermentation broth and purifying the produced neutral human milk oligosaccharide using a process for the purification of a neutral human milk oligosaccharide according to the invention.

In an embodiment, a solution, preferably a concentrated solution (a syrup) comprising the HMO is obtained, preferably an aqueous solution. Such syrup usually has an HMO content of at least 25 wt. %, preferably 25-50 wt. %, in particular of 25-35 wt. %. The syrup can e.g. by obtained by concentrating a purified solution obtained in accordance with the invention.

In an embodiment, the obtained product is in the form of a powder having a water content of less than 10 wt. %, preferably less than 8 wt. %, more preferably less than 5 wt. %. Typically the water content of such powder is in the range of 2 to 4%, based on dry matter (DM). The powder can e.g. by obtained by drying a syrup obtained in accordance with the invention.

In accordance with the invention a yield of 70% or more (based on HMO content in the fermentation broth) and a HMO purity of 90 wt. % or more (based on dry matter), in particular of 90-95 wt. % has been found feasible without the need for electrodialysis, without the need of active carbon, without the need for purification with nanofiltration or reverse osmosis, and needing only a single cycle of treatment with the cation exchange material, anion exchange material and adsorbent resin. In a preferred embodiment, the yield is in the range of 75-99 wt. %, in a specific embodiment in the range of 80-97 wt. % (based on HMO content in the fermentation broth).

In particular, the present invention allows to obtain 2'-fucosyllactose (herein further referred to as 2'-FL) from a fermentation broth, with a purity of 90 wt. % or more, based on dry matter. Preferably 2'-FL is obtained from the fermentation broth with a purity of 92 wt. % or more, more preferably 94 wt. % or more, even more preferably 95 wt. % or more, yet even more preferably 96 wt. % or more, yet even more preferably 97 wt. % or more and most preferably 98 wt. % or more, all based on dry matter. Preferably 2'-FL is obtained from the fermentation broth with a yield of 70% or more, more preferably 75% or more, even more preferably 80% or more, yet even more preferably 85% or more and most preferably 90% or more, all based on 2'-FL content in the fermentation broth. In a preferred embodiment the process according to the invention provides 2'-FL in a yield of 80% or more, based on 2'-FL content in the fermentation broth, with a purity of 90 wt. % or more, more preferably 92 wt. % or more, even more preferably 94 wt. % or more and most preferably 95 wt. % or more, based on dry matter. In a further preferred embodiment the process according to the invention provides 2'-FL in a yield of 85% or more, based on 2'-FL content in the fermentation broth, with a purity of 90 wt. % or more, more preferably 92 wt. % or more, even more preferably 94 wt. % or more, and most preferably 95 wt. % or more, based on dry matter.

Unless defined otherwise, all technical and scientific terms used herein have the same meaning as commonly understood by one of ordinary skill in the art.

The term "or" as used herein means "and/or" unless specified otherwise and unless it follows from the context that it must mean 'either . . . or'

The term "a" or "an" as used herein means "at least one" unless specified otherwise and unless it follows from the context that it must mean 'exactly one'.

When referring to a "noun" (e.g. a compound, an additive etc.) in singular, the plural is meant to be included, unless specified otherwise and unless it follows from the context that it must mean the singular form.

The term "about" in relation to a value generally includes a range around that value as will be understood by the skilled person. In particular, the range is from at least 10% below to at least 10% above the value, more specifically from 5% below to 5% above the value.

For the purpose of clarity and a concise description features are described herein as part of the same or separate embodiments, however, it will be appreciated that the scope of the invention may include embodiments having combinations of all or some of the features described.

A fermentation broth typically comprises a micro-organism or remains thereof, used for the production of the HMO, and nutrients for the micro-organisms. Residual carbon source from which the HMO is produced can also be present. Further, one or more side-products produced by the micro-organism may be present.

HMO's that can be recovered from a fermentation broth in accordance with a process according to the invention include neutral HMO's selected from the group of 2'-fucosyllactose (2'-FL), 3-fucosyllactose (3-FL), lacto-N-tetraose (LnT), 6'-galactosyllactose and 3'-galactosyllactose. A process according to the invention has been found particularly suitable to obtain purified 2'-FL from a fermentation broth.

The fermentative production of the HMO can be carried out based on known methodology for the microbiological production of oligosaccharides, e.g. as described in the prior art mentioned above or the prior art cited therein. Preferably lactose is used as a carbon source that is converted into HMO by the micro-organism in the fermentation broth. The fermentation broth containing HMO to be treated in step (i) of a process according to the invention usually has a total content of lactose of 0-0.20 wt. %, preferably of 0.01-0.15 wt. %, more preferably of 0.01-0.10 wt. %, in particular 0.02-0.07 wt. %, e.g. about 0.05 wt. % lactose.

Separation of biomass (step (i)) from the liquid phase (providing the crude solution comprising the HMO) can in principle be accomplished in a manner known per se for the type of fermentation broth that has been used to produce the HMO in. E.g. use can be made of clarification and/or filtration. Prior to step (i) the broth can be subjected to a degassing step. Such step can also be performed during or after step (i). Suitable degassing steps are generally known in the art. Degassing is advantageous in that it reduces the risk of the formation of gas bubbles during step (ii). Such gas bubbles could detrimentally affect effectiveness of step (ii); in case packed columns are used in step (ii) gas bubbles can disturb flow of the crude solution through the column and in case loose beads are used, gas formation could cause floating of the adsorbent material.

In accordance with the invention, the separation of biomass to obtain a crude HMO solution usually comprises a microfiltration step (MF). The MF is usually carried out with a membrane having a pore size of less than 1 μm, preferably of about 0.1 to about 0.2 μm. The MF (step (i)(a)) is particularly suitable to remove cell material (complete cells, fragments thereon and other supramolecular debris. MF can be performed at about ambient temperature. Usually the temperature is in the range of 20-75° C. Preferably, the MF is carried out at a temperature of at least 30° C., more preferably at a temperature in the range of 35–70° C. A relatively high temperature has been found advantageous for an increased yield of the HMO. In particular advantageous is a temperature in the range of about 40-50° C., such as a temperature of about 45° C., or a temperature in the range of about 60-70° C., such as about 65° C. Without being bound by theory, the inventors consider that excretion from the biomass into the liquid phase is improved at elevated temperature. Further, a high temperature, in particular a temperature of about 60° C. to 70° C. is advantageous for achieving a higher concentration factor of cell material during microfiltration, which has a positive effect on the yield of the HMO.

When combined with MF at a relatively high temperature, such as a temperature of at least about 45° C., heat treatment prior to UF can be an integrated part of the MF. For example, a high temperature, in particular a temperature of about 60° C. to 70° C., in combination with a recirculation of the MF retentate through a vented tank and/or receipt of MF permeate in a vented tank, results in a degassed MF permeate.

Furthermore, a high temperature, in particular a temperature of about 60° C. to 70° C., can modify protein, e.g. denature it, whereby it becomes less permeable through a UF membrane in a subsequent step.

Alternatively, if MF is performed at a temperature of about 20° C. to 50° C. (e.g. at 40-50° C., such as 45° C.), a heat treatment in combination with a venting tank may be performed as a separate step.

The permeate of the MF of step (i)(a) is preferably subjected to an ultrafiltration (UF) step (step (i)(b). The ultrafiltration step is particularly suitable to remove proteins, DNA and/or endotoxins from the permeate. Heat treatment serves to modify protein, e.g. denature it, whereby it becomes less permeable through the UF membrane. Step (i)(b) is usually carried out using a UF membrane having a cut-off of 5 kDa or less, in particular about 3 kDa or less. The cut-of usually is at least about 1 kDa.

In a preferred embodiment, the invention thus relates to a process for the purification of a neutral human milk oligosaccharide (HMO) from a fermentation broth, the process comprising the steps of:
  (i) separating biomass from the fermentation broth, the separation comprising the steps of:
    (a) microfiltration (MF); and
    (b) subjecting the MF permeate to ultrafiltration (UF) with a membrane having a molecular weight cut-off of 5 kDa or less;
  to provide a crude solution; and
  (ii) treating the crude solution with:
    (a) a cation-exchange material;
    (b) an anion-exchange material; and
    (c) a cation-exchange adsorbent resin;
thereby obtaining a purified solution containing the neutral human milk oligosaccharide.

In this preferred embodiment it is further preferred that the microfiltration in step (i)(a) is performed at a temperature in the range of 20-75° C., preferably in the range of 30-70° C., in particular in the range of 40-50° C. or in the range of 60-70° C. Optionally the MF permeate of step (i)(a) is subjected to a heat treatment before step (i)(b).

It is further preferred that the ultrafiltration in step (b) is performed with a membrane having a molecular weight cut-off 3 kDa or less, preferably of 3 kDa.

In order to increase HMO recovery from the broth, the MF of step (i)(a) and/or the UF of step (i)(b) may be applied with diafiltration.

Also in this embodiment the neutral human milk oligosaccharide is usually selected from the group consisting of 2'-fucosyllactose (2'-FL), 3-fucosyllactose (3-FL), lacto-N-tetraose (LnT), 6'-galactosyllactose and 3'-galactosyllactose. Preferably the neutral HMO is 2'-FL.

The crude solution obtained after separation of biomass from the liquid phase is treated with a cation exchange material (step (ii)(a)); an anion exchange material (step (ii)(b)); and a cation-exchange adsorbent resin (step (ii)(c)). It is generally preferred to at least carry out treatment with the cation exchange material and treatment with the anion exchange material subsequently. Particularly good results have been achieved with a process wherein the crude solution is first treated with the cation exchange resin, thereafter with the anion exchange resin and thereafter with the adsorbent resin.

An ion-exchange treatment can be a weak ion exchange treatment or a strong ion exchange treatment. The terms 'weak ion exchange' and 'strong ion exchange' are generally known in the art. A strong ion exchanger will not significantly lose the charge on its matrix once the ion exchanger is equilibrated and so a wide range of pH, generally from a strongly acidic pH to a strongly alkaline pH can be used. Weak ion exchangers have a more specific range of pH values in which they will maintain their charge, usually an acidic to about neutral pH in the case of weak anion exchange materials respectively an alkaline to about neutral pH in the case of weak cation exchange materials.

Ion exchange materials can e.g. be provided in packed columns, as membranes, as charge-modified depth filter cartridges or used as a material suspended or fluidized in a liquid that is to be treated with the ion exchange material. Ion exchange materials typically comprise a matrix provided with fixed functional groups (cationic for anion exchange materials, anionic for cation exchange materials). Examples of suitable ion exchange materials include fibrous gels, microcrystalline gels, or beaded gels. These may be made of e.g. any of the materials selected from polysaccharide based materials (e.g. agaroses, sepharoses, celluloses; silica-based materials, and organic polymeric matrix material (e.g. polyacrylamides, polystyrenes); that are derivatised to carry anionic or cationic groups.

The ion exchange materials can be employed in a manner known per se, e.g. as specified by the supplier, for a specific material of interest. A strong ion exchanger is advantageous over weak ion exchanger because of it's low pH dependence of the ion capture from the crude solution. An advantage of a weak ion exchanger is the easier regeneration, i.e. less chemicals are needed for regeneration, for a subsequent use.

The cation-exchange material is step (ii)(a) is used as a cation exchanger, i.e. for the removal of positively charged components. The cation-exchange step (ii)(a) preferably comprises treatment with a strong cation-exchange material. Preferably the cation-exchange material is a strong acid cation exchange material selected from the group consisting of styrene-divinylbenzene cation exchange resins, more preferably gel-type styrene-divinylbenzene cation exchange resins. Generally, cation-exchange (step (ii)(a)) is carried out using a cation-exchange material in the $H^+$ form. In particular, good results have been achieved with a cation-exchange material comprising sulfonic acid functional groups. Most preferably the cation-exchange material is a strong acid cation exchange resin having a styrene/divinylbenzene gel-type matrix and sulfonic acid functional groups.

The anion-exchange material is step (ii)(b) is used as an anion exchanger, i.e. for the removal of negatively charged components. The anion-exchange (step (ii)(b)) preferably comprises treatment with a weak anion-exchange material. Of a weak anion-exchange material it has been found that it does not substantially adsorb 2'-FL or another HMO, under conditions where it binds anions from the fermentation broth. It is advantageously used to remove traces of DNA. When using a strong anion-exchange material adsorption of HMO may be a problem, at least in some embodiments. Thus, use of a weak anion-exchange material can contribute to a particularly high HMO yield. Generally, anion-exchange (step (ii)(b)) is carried out using an anion-exchange material in the OH form. Preferably, the anion-exchange material is a weakly basic anion exchange resin selected from the group consisting of cross-linked acrylic based weak anion exchange resins, preferably gel-type cross-linked acrylic based weakly basic anion exchange resins. In particular, good results have been achieved with an anion-exchange material comprising tertiary amine functional groups. Most preferably the weakly basic anion exchange material is a cross-linked acrylic based anion exchange resin, preferably a gel-type cross-linked acrylic based anion exchange resin, having tertiary amine functional groups.

The adsorbent resin in step (ii)(c) is also a cation-exchange type of material. In a process according to the invention it is used to adsorb components from the fermentation broth, typically organic components, in particular non-cationic components, more in particular components, other than HMO, that are neutral at the pH of the broth. An advantage of such material, e.g., over activated carbon is its inertness towards adsorption of neutral oligosaccharides. Surprisingly, the cation-exchange adsorbent resin has been found suitable to also remove colour from the solution containing HMO. In particular it has been found effective in removing Maillard reaction products and aldol reaction products. The adsorbent resin of step (ii)(c)—which is preferably used after the cation-exchange (step (ii)(a)) and the anion-exchange (step (ii)(b))—is also capable of removing (residual) cations originating from the broth. The adsorbent resin in step (ii)(c) is thus used for removal (via adsorption) of components, in particular neutral components, other than HMO. Preferably the cation-exchange adsorbent resin is a poly-aromatic adsorbent resin, provided with sulfonic acid functional groups in order to increase the hydrophilicity. The resin matrix is preferably styrene-divinyl benzene copolymer based. The resin is generally highly porous. More preferably the adsorbent resin is highly porous and has a styrene/divinyl benzene copolymer matrix of which the hydrophilicity is increased by the presence of sulphonic acid groups. The porosity is preferably about 0.8 to 1.2 ml/g, more preferably about 0.9 to about 1.1 ml/g, even more preferably about 0.95 to about 1.05 ml/g, and most preferably about 1.0 ml/g, and the average surface area is preferably more than ≥600 $m^2/g$, more preferably ≥650 $m^2/g$, even more preferably ≥670 $m^2/g$ and most preferably ≥700 $m^2/g$. In a particularly preferred embodiment the porosity is about 1.0 ml/g and the average surface area ≥700 m²/g. Such adsorbent resins are commercially available.

The present invention thus relates to a process for the purification of a neutral human milk oligosaccharide (HMO) from a fermentation broth, the process comprising the steps of:
(i) separating biomass from the fermentation broth to provide a crude solution;
(ii) treating the crude solution with:
   (a) a cation-exchange material, for the removal of positively charged components;
   (b) an anion-exchange material, for the removal of negatively charged components; and
   (c) a cation-exchange adsorbent resin, for adsorption of components, in particular neutral components, other than HMO;
thereby obtaining a purified solution containing the neutral human milk oligosaccharide. The cation-exchange adsorbent resin of step (ii)(c) preferably has a porosity of about 0.8 to 1.2 ml/g and an average surface area of ≥600 m²/g.

The order of steps (ii)(a) and (ii)(b) may also be reversed, i.e. the treatment with the weakly basic anion exchange resin of step (ii)(b) may be performed before or after the treatment with the strong acid cation-exchange resin of step (ii)(a). The order of treatments (a), (b) and (c) in step (ii) may thus be (a) followed by (b) followed by (c), or alternatively (b) followed by (a) followed by (c).

In a preferred embodiment of step (ii) of the process according to the invention, the crude solution obtained in step (i) is treated with:
(ii)(a) a strong acid cation-exchange resin, preferably a strong acid cation exchange resin having a styrene/divinylbenzene gel-type matrix and sulfonic acid functional groups;
(ii)(b) a weakly basic anion-exchange resin, preferably a weakly basic anion exchange resin having a cross-linked acrylic gel-type matrix and tertiary amine functional groups; and
(ii)(c) a cation-exchange adsorbent resin, preferably a cation-exchange adsorbent resin having a styrene/divinylbenzene copolymer matrix and sulfonic acid functional groups.

In this embodiment it is further preferred that step (i) comprises (i)(a) MF, followed by (i)(b) UF of the MF permeate to obtain the crude solution, and step (ii)(c) follows after steps (ii)(a) and (ii)(b). In particular good results have been obtained with a process wherein step (i) comprises (i)(a) MF, followed by (i)(b) UF of the MF permeate to obtain the crude solution, and that first the cation exchange step (ii)(a) with said strong acid cation-exchange resin is carried out, thereafter the anion exchange step (ii)(b) with said weakly basic anion-exchange resin and thereafter the adsorption step with (ii)(c) with the cation-exchange adsorbent resin is carried out.

In this embodiment it is further preferred that the porosity of the cation-exchange adsorbent resin in step (ii)(c) is about 0.8 to 1.2 ml/g, more preferably about 0.9 to about 1.1 ml/g, even more preferably about 0.95 to about 1.05 ml/g, and most preferably about 1.0 ml/g, and that the average surface area is preferably more than ≥600 m²/g, more preferably ≥650 m²/g, even more preferably ≥670 m²/g and most preferably ≥700 m²/g. In a particularly preferred embodiment the porosity is about 1.0 ml/g and an average surface area ≥700 m²/g.

In a particularly preferred embodiment, the invention relates to a process for the purification of a neutral human milk oligosaccharide (HMO) from a fermentation broth, the process comprising the steps of:
(i) separating biomass from the fermentation broth, the separation comprising the steps of:
   (a) microfiltration (MF), optionally with diafiltration; and
   (b) subjecting the MF permeate to ultrafiltration (UF) with a membrane having a molecular weight cut-off of 5 kDa or less, optionally with diafiltration;
to provide a crude solution; and
(ii) treating the crude solution with:
   (a) a strong acid cation-exchange resin, preferably a strong acid cation exchange resin having a styrene/divinylbenzene gel-type matrix and sulfonic acid functional groups;
   (b) a weakly basic anion-exchange resin, preferably a weakly basic anion exchange resin having a cross-linked acrylic gel-type matrix and tertiary amine functional groups; and
   (c) a cation-exchange adsorbent resin, preferably a cation-exchange adsorbent resin having a styrene/divinylbenzene copolymer matrix and sulfonic acid functional groups.

thereby obtaining a purified solution containing the neutral human milk oligosaccharide. More preferably the porosity of the cation-exchange adsorbent resin in step (ii)(c) is about 0.8 to 1.2 ml/g, more preferably about 0.9 to about 1.1 ml/g, even more preferably about 0.95 to about 1.05 ml/g, and most preferably about 1.0 ml/g, and that the average surface area is preferably more than ≥600 m²/g, more preferably ≥650 m²/g, even more preferably ≥670 m²/g and most preferably ≥700 m²/g. Even more preferably the cation-exchange adsorbent resin has a porosity of about 1.0 ml/g and an average surface area of ≥700 m²/g.

Also in this embodiment of the process according to the invention the neutral human milk oligosaccharide is usually selected from the group consisting of 2'-fucosyllactose (2'-FL), 3-fucosyllactose (3-FL), lacto-N-tetraose (LnT), 6'-galactosyllactose and 3'-galactosyllactose. Most preferably the neutral HMO is 2'-FL.

It is usually sufficient to subject the crude solution to a single (sequence) of treatment with the anion-exchange material, the cation-exchange material and the adsorbent resin to obtain a purified solution containing the neutral human milk oligosaccharide. If desired, the purified solution may be further treated, e.g. further purified and/or concentrated. Such further treatment preferably comprises at least one treatment selected from the group consisting of nanofiltration (NF) and reverse osmosis (RO). NF or RO treatment is typically used to remove water, thereby concentrating the HMO. If a high flux is desired (requiring less membrane area) NF is considered to be particularly suitable. RO, operated at a relatively high pressure has been found particularly suitable for obtaining a highly concentrated syrup with a high HMO content, such as a HMO content of 35-50 wt. %.

Alternatively or in addition the purified solution may be subjected to an evaporation step to concentrate the solution, e.g. to obtain a concentrated solution (a syrup).

In a specific embodiment, after treating the crude solution in step (ii), the purified solution containing the HMO is subjected to an additional polishing step. For this an adsorbent material, such as activated carbon, can be used. If the purified solution is further to be subjected to a concentration step, the polishing step is usually carried out before the concentration step. It is particular useful to further reduce organic compounds, if desired, and/or to remove residual colour, if desired.

In a specific embodiment, after treating the crude solution in step (ii), the purified solution containing the HMO is subjected to an additional polishing step. For this an adsorbent material, such as a charge-modified depth filter can be used. If the purified solution is further to be subjected to a concentration step, the polishing step is usually carried out before the concentration step. It is particular useful to reduce potentially residual DNA fragments.

In a specific embodiment, the concentration step (e.g. by NF, RO or evaporation), is followed by a sterilizing grade microfiltration step to ensure that no germs or spores are present in the solution, In an advantageous embodiment of the process according to the invention, the purified solution (optionally after a concentration treatment) is subjected to a crystallisation step to obtain a crystalline HMO. Suitable crystallisation conditions can be based on those known in the art for oligosaccharides in general, or an HMO of interest in particular.

In an advantageous embodiment of the process according to the invention, the purified solution (optionally after a concentration treatment) is subjected to a drying step to obtain HMO in powder form. Suitable drying conditions can be based on those known in the art for oligosaccharides in general, or an HMO of interest in particular. Preferred drying steps include spray-cooling, spray drying and lyophilisation (freeze-drying). In particular good results have been achieved with spray-drying.

The invention will now be illustrated by the following examples.

EXAMPLE 1

2'-FL was produced by microbiological conversion of glucose to GDP-fucose followed by intracellular enzymatic transfer to lactose in an alpha-1,2-linkage. The reaction was catalyzed by fucosyltransferase present in an engineered host strain of $E.\ coli$ K12 bacteria, at 30° C. in a fermentation broth, generally as described in WO 2012/112777 and WO 2014/018596, with the difference that glycerol was replaced by glucose and DF204 antifoam by Basildon 98/007K. The other components in the fermentation broth include ammonium, sodium, magnesium, phosphate, potassium, sulphate, antifoaming agents, nitrilotriacetic acid (NTA) and trace elements.

Demineralized water is used for highest purity. Temperature, pH, and dissolved oxygen are controlled within defined limits during the fermentation process.

The fermentation was started with 1000 liter sterilized medium and continued until 3.52% 2'-FL had formed.

The resultant broth containing 2'-FL was subjected to (ia) microfiltration, to remove the cells, using a membrane having a membrane area of 10.8 m² and a 0.1 μm cut-off.

Operational Data MF:

| Mass fermentation broth | 2028 kg |
|---|---|
| Recirculation flow | 6000-6500 L/hr |
| TMP | 1.8 |
| Temperature | 45° C. |
| Diafiltration | 80% of feed |
| Start diafiltration at VCR | 1.7 |
| Final concentration VCR | 2.5 |

Details MF:

| Measurements | Total kg | Protein according to Bradford assay | Kg 2'-FL |
|---|---|---|---|
| Fermentation broth | 2028 | 1.6 | 69.4 |
| diawater added | 1600 | | |
| Final retentate | 800 | 3.0 | 6.7 |
| Final permeate | 3080 | <0.2 | 61.60 |
| Deviation in mass balance | 252 kg* | | 2% |

*(or less diawater is added)

Based on the total amount of 2'-FL present after MF, the yield over the MF was calculated as: 91%.

The chemical analysis was as follows:

| On dry matter (DM) | | liquid |
|---|---|---|
| DM | % | 2.71 |
| 2'-FL/DM | % | 74% |
| Ash/DM | % | 8.1 |
| Protein according to Bradford assay/DM | ppm | 12657 |
| HPLC intern/DM | % | 4.03 |
| Minerals LQS (sum) | % | 4.30 |
| Heavy metals | ppm | 2.77 |
| Organic acids (sum) | % | 13.99 |

Next, the permeate of the MF was subjected to (ib) ultrafiltration, to remove protein and minerals, using 2×7 m² membrane area, the membrane having a cut-off of 5 kDa.

Operational Data

| Mass MF permeate | 3080 kg |
|---|---|
| Recirculation flow | 2000 L/hr |
| TMP | 1.6 |
| Temperature | 14-15° C. |
| Diafiltration | 500 kg |
| Start diafiltration at VCR | 250 kg IBC - 12 |
| Final concentration VCR | 150 kg IBC - 20 |

Details UF:

| | Total kg | Protein assay Acc. to Bradford | BRIX | OD420 | OD450 | % 2'-FL | Kg 2'-FL |
|---|---|---|---|---|---|---|---|
| MF permeate | 3080 | <0.2 | | | 2.005 | 2.0 | 62.0 |
| MF-P-EOC (measured 23/02) | | | 3.0 | 3.14 | | | |
| Diawater added | 500 | | | | | | |
| Final retentate | 150 | 0.3 | | | 1.345 | 0.48 | 0.7 |
| UF perm ex diaw | | | 2.6 | 2.63 | | | |
| Final UF permeate | 3430 | <0.2 | | | 1.049 | 1.79 | 61.4 |
| Deviation in mass balance | 0 | | | | | | 0.1 |

The 2'-FL yield of UF was 99%.

For the OD450 a reduction of a factor 2 was reached. This was mainly achieved by the UF. The ultrafiltration blocked part of the (color) components reducing already a part of the color that needed to be removed otherwise in the subsequent steps.

| UF permeate on DM | | |
| --- | --- | --- |
| % DM | % | 2.44 |
| 2'-FL/DM | % | 78 |
| Ash/DM | % | 7.8 |
| Protein assay acc. to Bradford/DM | ppm | 451 |
| Minerals (sum) | % | 4.34 |
| Heavy metals | ppm | 2.1 |
| Organic acids (sum) | % | 14.63 |

The main reduction of components was seen in the protein level as quantified with the Bradford assay. The level of Bradford in the MF permeate was 12000 ppm. This was reduced in the UF permeate to 600 ppm (both on total dry matter).

Thereafter, the crude solution of HMO (permeate of UF) was subjected subsequently to
(iia) cation exchange in 280 l column of a strong acid cation exchange resin having a styrene/divinylbenzene gel-type matrix and sulfonic acid functional groups;
(iib) anion exchange in 225 l column of a weakly basic anion exchange resin having a cross-linked acrylic gel-type matrix and tertiary amine functional groups;
(iic)) adsorption on adsorbent resin in 280 l of a cation exchange adsorbent resin having a styrene/divinylbenzene copolymer matrix and sulfonic acid functional groups, and having a porosity of about 1.0 ml/g and an average surface area of ≥700 m$^2$/g.

Before passing the crude solution through the columns, the columns were first rinsed with water for about 60 min (at about 1100 l/hr).

The crude solution was passed through the columns at a rate of 1100 l/hr. at the outlet of the last column (iic), the eluent was monitored for its 2'-FL content, using BRIX (a generally known measure for saccharide content of a solution). Once the BRIX value reached 0.2, collection of eluent (containing 2'-FL) was started. Collection continued till BRIX dropped. The collected eluent was a purified solution containing the neutral human milk oligosaccharide.
data after step (iic):

| | Total kg | pH | Bradford | Cond mS/cm | BRIX | OD450 | % 2'-FL | Kg 2'-FL |
| --- | --- | --- | --- | --- | --- | --- | --- | --- |
| feed | 3350 | 6.7 | <0.2 | 2.54 | 2.57 | 1.049 | 1.79 | 59.6 |
| Collected eluent | 3630 | 4.4 | <0.2 | 0.028 | 1.7 | | 1.63 | 59.2 |
| | +10% dilution | | | | | | | |

Based on the analytical data of 2'-FL and the total quantity of UF permeate and collected eluent, the 2'-FL yield of steps (iia)-(iic) was 99%.

Thereafter, the collected eluent was further treated by NF to remove water (concentration of 2'-FL).
Process Data:

| Volume NF retentate | 178 |
| --- | --- |
| Recirculation flow | 1400 |
| Pressure | 30 |
| Temperature | 6-10 |
| Final concentration VCR | 31 BRIX |

The 2'-FL was concentrated from 1.7 BRIX to 32 BRIX. 2'-FL content was increased from 1.63% to 28.6%. Conductivity increased from 28 to 123 uS/m. OD290 (organics) and OD420 (colour) after concentration remained low at 0.356 and 0.002 respectively.

Chemical Analysis

| NF retentate on DM | | liquid |
| --- | --- | --- |
| % DM | % | 32 |
| 2'-FL/DM | % | 91 |
| Ash/DM | % | 0.1 |
| Bradford/DM | ppm | 59 |
| Heavy metals | ppm | |
| Organic acids (sum) | % | |

The concentrate obtained after NF, having a dry matter content of 32% was subsequently subjected to a pasteurization step and the pasteurized concentrate was spray dried to obtain a 2'-FL powder.

The overall yield starting from the broth was 83%.

EXAMPLE 2

A fermentation broth obtained in a manner essentially as described in Example 1 was subjected to pasteurization (80° C., 15 sec), and subjected to steps (ia), (ib), (iia), (iib) and (iic), essentially as described in Example 1. The eluent from step (iic) was collected as long as BRIX was larger than 0.1. The eluent was subjected to RO instead of NF

| RO | mass [kg] | Brix | pH | Conductivity [mS/cm] | 2'-FL | Bradford | Amount 2'-FL kg |
| --- | --- | --- | --- | --- | --- | --- | --- |
| RO feed | 583 | 2.2 | 4.68 | 0.006 | 1.8 | 12 | 10.5 |
| RO retentate after displacement | 46 | 25.3 | 3.75 | 0.030 | 21.4 | 18 | 9.8 |
| RO permeate as is | 542 | 0.0 | 5.64 | 0.002 | 0.3 | 6 | 1.6 |

There amount of retentate was too low to concentrate to >30 Brix. The 2'-FL yield was 93%.

EXAMPLE 3

3-fucosyllactose (3-FL) was produced by microbiologial conversion of glucose to GDP-fucose followed by intracellular enzymatic transfer to lactose in an alpha-1,3-linkage. The reaction was catalyzed by fucosyltransferase present in an engineered host strain of E. coli in a fermentation broth, generally as described in WO 2012/112777.

The fermentation broth comprising 3-FL was subjected to steps (i), (iia), (iib) and (iic), essentially as described in Example 1 above. Measurements of Brix, conductivity and color of the product showed a much increased purity of the 3-FL solution.

Data after Step (ii)(c)

|  | Brix | Conductivity (mS/cm) | OD420 |
|---|---|---|---|
| Fermentation broth | 8.4 | 27.9 | 4.64 |
| Purified solution after step (ii)(c) | 1.9 | 0.080 | 0.008 |

EXAMPLE 4

Lacto-N-tetraose (LNT) was produced as described in WO 2014/153253. The fermentation broth comprising LNT was subjected to steps (i), (iia), (iib) and (iic), essentially as described in Example 1 above. Measurements of Brix, conductivity and color of the product showed a much increased purity of the LNT solution.

Data after step (ii)(c)

|  | Brix | Conductivity (mS/cm) | OD420 |
|---|---|---|---|
| Fermentation broth | 4.6 | 11.48 | 1.66 |
| Purified solution after step (ii)(c) | 0.4 | 0.012 | −0.004 |

The invention claimed is:

1. A process for purifying a neutral human milk oligosaccharide (HMO) from a fermentation broth, the process comprising:
   (i) separating biomass from the fermentation broth to provide a crude solution;
   (ii) treating the crude solution with:
      (a) a cation-exchange material;
      (b) an anion-exchange material; and
      (c) a cation-exchange adsorbent resin for adsorbing components other than HMO that are neutral at the pH of the broth and/or to remove color,
   thereby obtaining a purified solution containing the neutral human milk oligosaccharide.

2. The process according to claim 1, wherein the neutral human milk oligosaccharide is selected from the group consisting of 2'-fucosyllactose (2'-FL), 3-fucosyllactose (3-FL), lacto-N-tetraose (LnT), 6'-galactosyllactose and 3'-galactosyllactose.

3. The process according to claim 1, wherein the cation exchange material is selected from the group consisting of gel-type styrene/divinylbenzene cation exchange resins.

4. The process according to claim 1, wherein the cation exchange material is an acid cation exchange resin having a styrene/divinylbenzene gel-type matrix and sulfonic acid functional groups.

5. The process according to claim 1, wherein the anion exchange material is selected from the group consisting of cross-linked acrylic based anion exchange resins.

6. The process according to claim 1, wherein the anion exchange material is a gel-type cross-linked acrylic based anion exchange resin, having tertiary amine functional groups.

7. The process according to claim 1, wherein the cation-exchange adsorbent resin has a styrene/divinylbenzene copolymer matrix and sulfonic acid functional groups, a porosity of about 0.8 to 1.2 ml/g and an average surface area of ≥600 m$^2$/g.

8. The process according to claim 1, wherein the crude solution is treated first with the cation exchange material, thereafter with the anion exchange material and thereafter with the adsorbent resin.

9. The process according to claim 1, wherein the separating comprises:
   (a) microfiltration (MF) to obtain a MF permeate; and
   (b) subjecting the MF permeate to ultrafiltration with a membrane having a molecular weight cut-off of 5 kDa or less.

10. The process according to claim 9, wherein the ultrafiltration is performed with a membrane having a molecular weight cut-off of 3 kDa or less.

11. The process according to claim 9, wherein the microfiltration is performed at a temperature in the range of 20-75° C.

12. The process according to claim 9, wherein the microfiltration is performed at a temperature in the range of 30-70° C.

13. The process according to claim 9, wherein the MF permeate is subjected to a heat treatment before ultrafiltration.

14. The process according to claim 9, further comprising:
   (iii) subjecting the purified solution to nanofiltration or reverse osmosis.

15. The process according to claim 1, further comprising (iii) drying or crystallizing the purified solution.

16. The process according to claim 15, wherein drying is by spray drying.

17. The process according to claim 1, wherein the neutral human milk oligosaccharide is obtained in the form of a powder having a water content of less than 10 wt. % and having a purity of 90 wt. % or more.

18. The process according to claim 1, wherein the neutral human milk oligosaccharide is obtained in the form of a powder having a water content of less than 8 wt. % and having a purity of 92 wt. % or more.

19. The process according to claim 1, wherein the neutral human milk oligosaccharide is obtained in the form of a syrup.

20. The process according to claim 1, which does not comprise an electrodialysis step.

21. The process according to claim 1, wherein the purified solution is further subjected to a treatment with a polishing material.

22. A method for producing a neutral human milk oligosaccharide, comprising producing the neutral human milk oligosaccharide by microbial fermentation in a fermentation broth and purifying the produced neutral human milk oligosaccharide using a process according to claim 1.

23. The process according to claim 1, wherein the cation-exchange adsorbent resin adsorbs organic components.

* * * * *